(12) United States Patent
Kariv (10) Patent No.: US 10,441,193 B2
(45) Date of Patent: *Oct. 15, 2019

(54) DISTRIBUTED LOCATION SENSOR

(71) Applicant: St. Jude Medical International Holding S.à r.l., Luxembourg, LU, Luxembourg (LU)

(72) Inventor: Itay M. Kariv, Haifa (IL)

(73) Assignee: St. Jude Medical International Holding S.à r.l., Luxembourg (LU)

( * ) Notice: Subject to any disclaimer, the term of this patent is extended or adjusted under 35 U.S.C. 154(b) by 200 days.

This patent is subject to a terminal disclaimer.

(21) Appl. No.: 15/292,773

(22) Filed: Oct. 13, 2016

(65) Prior Publication Data

US 2017/0027476 A1    Feb. 2, 2017

Related U.S. Application Data

(63) Continuation of application No. 13/748,196, filed on Jan. 23, 2013, now Pat. No. 9,468,397.

(51) Int. Cl.
*A61B 5/06* (2006.01)
*A61B 18/14* (2006.01)
(Continued)

(52) U.S. Cl.
CPC ............... *A61B 5/062* (2013.01); *A61B 5/06* (2013.01); *A61B 5/065* (2013.01);
(Continued)

(58) Field of Classification Search
CPC .......... A61M 25/0067; A61M 25/0068; A61M 25/0069; A61M 25/10; A61M 25/0631;
(Continued)

(56) References Cited

U.S. PATENT DOCUMENTS 6,161,032 A    12/2000  Acker
6,233,476 B1    5/2001  Strommer et al.
(Continued)

OTHER PUBLICATIONS

Perna et al., "Assessment of Catheter Tip Contact Force Resulting in Cardiac Perforation in Swine Atria Using Force Sensing Technology," Circulation: Arrhythmia and Electrophysiology Journal of the American Heart Association, Jan. 2011 [online] [Retrieved from the internet: ,URL:http://circep.ahajournals.org>.
(Continued)

*Primary Examiner* — Aaron B Fairchild
(74) *Attorney, Agent, or Firm* — Dykema Gossett PLLC (57) ABSTRACT

A catheter configured for use with a magnetic field-based localization system includes a distributed location sensor that includes a plurality of individual location sensing coils electrically connected in series. The distributed location sensor has an effective magnetic center based on the individual characteristics of each location sensing coil. The effective magnetic center can be located in a space occupied by another structure such as an irrigation fluid delivery tube. The plurality of individual location sensing coils are generally smaller, thereby easing placement, and collectively, when connected in series, output a relatively strong and noise-free signal.

14 Claims, 8 Drawing Sheets

(51) Int. Cl.
  *A61B 34/20* (2016.01)
  *A61B 90/00* (2016.01)
  *A61B 18/00* (2006.01)
(52) U.S. Cl.
  CPC .......... *A61B 18/1492* (2013.01); *A61B 34/20* (2016.02); *A61B 90/37* (2016.02); *A61B 5/061* (2013.01); *A61B 2018/00029* (2013.01); *A61B 2018/00577* (2013.01); *A61B 2034/2051* (2016.02); *A61B 2090/376* (2016.02); *A61B 2217/007* (2013.01); *A61B 2218/002* (2013.01)
(58) Field of Classification Search
  CPC ........ A61B 2218/002; A61B 2217/007; A61B 5/061; A61B 5/062; A61B 5/065; A61B 2034/2051
  See application file for complete search history.

(56) References Cited

U.S. PATENT DOCUMENTS

| | | |
|---|---|---|
| 6,253,770 B1 | 7/2001 | Acker et al. |
| 6,498,944 B1 | 12/2002 | Ben-Haim et al. |
| 6,593,884 B1 | 7/2003 | Gilboa et al. |
| 6,788,967 B2 | 9/2004 | Ben-Haim et al. |
| 7,229,437 B2 | 6/2007 | Johnson et al. |
| 7,386,339 B2 | 6/2008 | Strommer et al. |
| 7,816,915 B2 | 10/2010 | Susel et al. |
| 7,881,769 B2 | 2/2011 | Sobe |
| 8,060,185 B2 | 11/2011 | Hunter et al. |
| 8,147,486 B2 | 4/2012 | Honour et al. |
| 8,187,267 B2 | 5/2012 | Pappone et al. |
| 2001/0021840 A1* | 9/2001 | Suresh .............. A61M 25/0068 604/525 |
| 2008/0294158 A1 | 11/2008 | Pappone et al. |
| 2010/0152731 A1 | 6/2010 | de la Rama et al. |
| 2010/0317961 A1 | 12/2010 | Jenkins |
| 2010/0324412 A1 | 12/2010 | Govari et al. |

OTHER PUBLICATIONS

Thompson, Heather, "MD+DI's Manufacturer of the Year: Johnson & Johnson," Oct. 27, 2011 [Retrieved from the internet: <URL:http://www.mddionline.com/print/8507>.

* cited by examiner

DISTRIBUTED LOCATION SENSOR

CROSS-REFERENCE TO RELATED APPLICATIONS

This application is a continuation of U.S. application Ser. No. 13/748,196, filed 23 Jan. 2013 (the '196 application), now pending. The '196 application is hereby incorporated by reference as though fully set forth herein.

BACKGROUND a. Technical Field

The instant disclosure relates generally to location sensors and more particularly to a distributed location sensor for use in a medical device.

b. Background Art

Medical devices such as guidewires, catheters, introducers and the like with magnetic field-based position sensors for device navigation are used in various medical procedures in the body. Typically, a magnetic field position sensor includes a generally cylindrical coil that transforms an applied magnetic field into an induced voltage. This induced voltage is used by an upstream localization system to compute the sensor's spatial position and orientation. For example only, it is known to equip a catheter with one or more coils sufficient to allow detection of five (5) or six (6) degrees-of-freedom (DOF), namely, a three-dimensional (3D) position (X, Y, Z) and two or three orientation parameters (e.g., roll, pitch, yaw).

In practice, repeatable and accurate location computation by the localization system is dependent on the availability of a clear induced voltage (i.e., a signal having a good signal to noise ratio). Moreover, there is a linear correlation between the sensor size and the induced voltage (and/or current) yielded by the sensor. Thus, with the ongoing process of miniaturization of such coil sensors, limits are being reached where the induced voltages are inadequate for use in repeatable and accurate location computations.

The foregoing discussion is intended only to illustrate the present field and should not be taken as a disavowal of claim scope.

SUMMARY

According to various embodiments, at least one advantage of a medical device that includes a distributed location sensor is increased design flexibility as to the placement of the components of the sensor without compromise of the quality of the induced signal that is indicative of the location of the sensor.

In an embodiment, a medical device configured for use with a magnetic field-based localization system includes a shaft, an electrode, an obstruction, and a distributed location sensor. The shaft has a proximal end portion and distal end portion. The electrode is located at the distal end portion of the shaft. The obstruction is located on or in the shaft and is selected from the group comprising a fluid delivery lumen, a pull wire lumen, a pull wire, a pull ring, a twisted pair cable, an irrigation passageway, a temperature sensor and electrical wiring. The distributed location sensor includes a plurality of location sensing coils electrically connected in series and disposed in the distal end portion of the shaft. The plurality of location sensing coils has an effective magnetic center located in a space occupied by the obstruction. The distributed location sensor is configured to produce a signal responsive to an applied magnetic field produced by the localization system where the signal is indicative of a location of the effective magnetic center.

In an embodiment, a medical device configured for use with a magnetic field-based localization system includes a shaft, a tip electrode, a fluid delivery lumen and a distributed location sensor. The shaft has a proximal end portion and distal end portion. The tip electrode has an irrigation passageway with a fluid inlet and at least one outlet on an outer surface of the electrode. The fluid delivery lumen is coupled at one end to the fluid inlet and is configured to be coupled to an irrigation fluid delivery system. The distributed location sensor includes a plurality of location sensing coils electrically connected in series and disposed in the distal end portion. The plurality of location sensing coils has an effective magnetic center located in a space occupied by the fluid lumen delivery lumen. The distributed location sensor is configured to produce a signal responsive to an applied magnetic field produced by the localization system where the signal is indicative of a location of the effective magnetic center.

The foregoing and other aspects, features, details, utilities, and advantages of the present disclosure will be apparent from reading the following description and claims, and from reviewing the accompanying drawings.

DETAILED DESCRIPTION

Various embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment," or the like, means that a particular feature, structure, or characteristic described in connection with the embodiment is included in at least one embodiment. Thus, appearances of the phrases "in various embodiments," "in some embodiments," "in one embodiment," or "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a clinician manipulating one end of a medical device or instrument used to treat a patient. The term "proximal" refers to the portion of the device closest to the clinician (or to a robotic control configured to manipulate the device) and the term "distal" refers to the portion located furthest from the clinician. It will be further appreciated that for conciseness and clarity, spatial terms such as "vertical," "horizontal," "up," and "down" may be used herein with respect to the illustrated embodiments. However, medical devices may be used in many orientations and positions, and these terms are not intended to be limiting or absolute.

Figure 1:
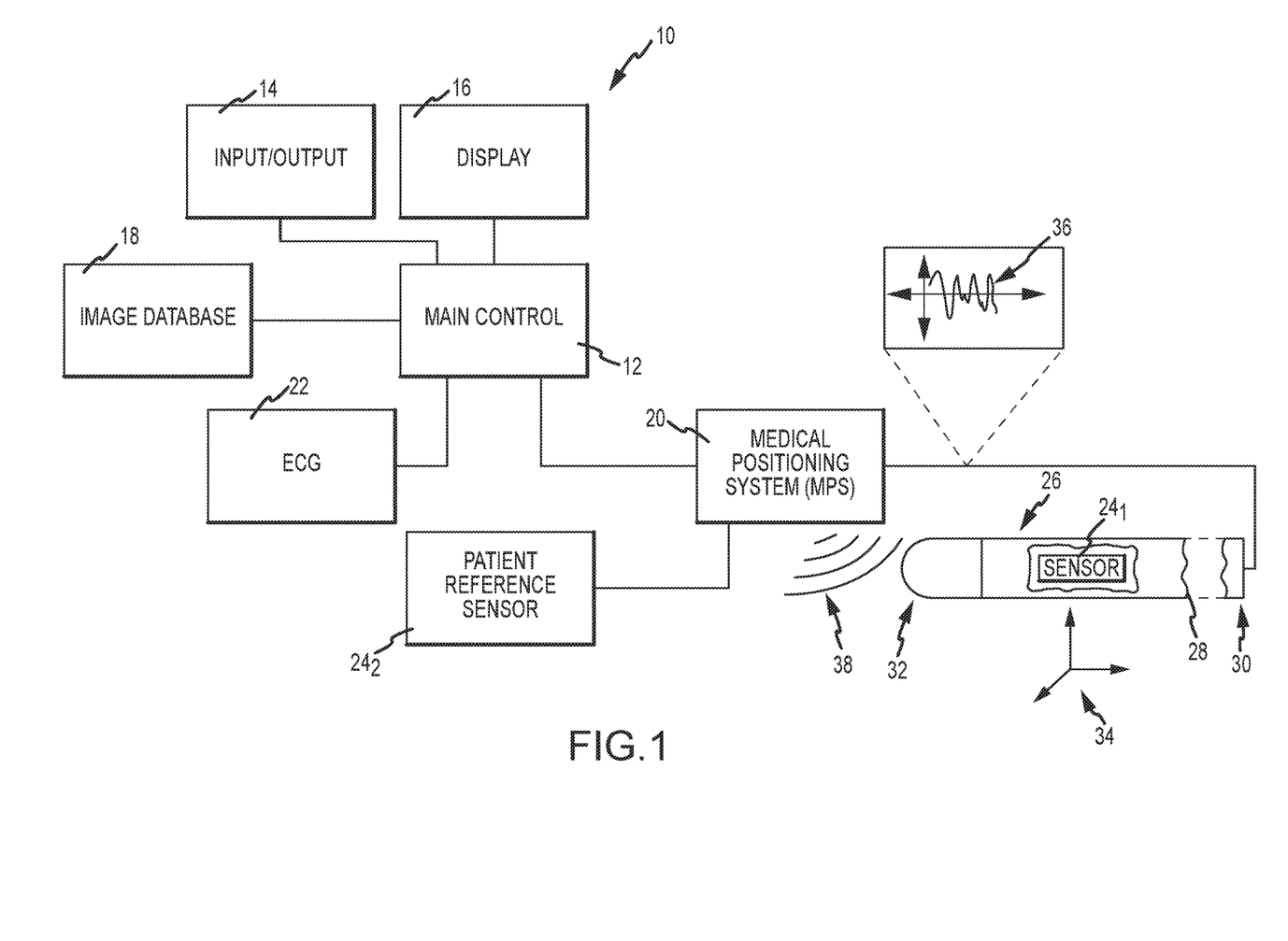
FIG. 1 is a schematic and block diagram view of a system illustrating an environment in which a medical device having a distributed location sensor may be used.

Before proceeding to a detailed description of a distributed location sensor, a general description will first be set forth of an exemplary system (FIGS. 1-2) in which a medical device with such a distributed location sensor may be used. Referring now to the drawings wherein like reference numerals are used to identify identical or similar components in the various views, FIG. 1 is a diagrammatic and block diagram view of a system 10 that includes a medical device 26. Medical device 26 may include any one of a wide range of invasive medical devices, such as those devices configured for diagnostic, therapeutic and/or delivery purposes.

Medical device 26, such as a catheter, may be configured to perform various tracking, navigation, orientation and other location-related functions (e.g., using the catheter's location for superimposing a representation thereof on imaging of a region of interest). These functions are facilitated where the device is configured to allow a localization system to determine its position and/or orientation. As described in the Background, such devices, in magnetic field-based positioning embodiments, are typically configured to include one or more location sensors, for example, a magnetic field-based location sensing coil.

System 10 as depicted includes a main electronic control unit 12 (e.g., one or more electronic processors) having various input/output mechanisms 14, a display 16, an optional image database 18, a localization system such as a medical positioning system (MPS) 20, an electrocardiogram (ECG) monitor 22, a distributed location sensor $24_1$, an optional patient reference sensor (PRS) $24_2$, and an MPS-enabled elongate medical device 26. As shown, medical device 26 includes a main body 28 (e.g., a shaft) having a longitudinal axis, and which includes a proximal end portion 30 and a distal end portion 32.

Input/output mechanisms 14 may comprise conventional apparatus for interfacing with a computer-based control unit, for example, a keyboard, a mouse, a tablet, a foot pedal, a switch or the like. Display 16 may also comprise conventional apparatus.

Medical device 26 may find use in navigation applications that use imaging of a region of interest. Therefore system 10 may optionally include image database 18. Image database 18 may be configured to store image information relating to the patient's body, for example, a region of interest surrounding a destination site for medical device 26 and/or multiple regions of interest along a navigation path contemplated to be traversed by device 26 to reach the destination site. The image data in database 18 may comprise known image types including (1) one or more two-dimensional still images acquired at respective, individual times in the past (pre-acquired imaging); (2) a plurality of related two-dimensional images obtained in real-time from an image acquisition device (e.g., fluoroscopic images from an x-ray imaging apparatus, such as that shown in exemplary fashion in FIG. 2) wherein the image database acts as a buffer (live fluoroscopy); and/or (3) a sequence of related two-dimensional images defining a cine-loop (CL) wherein each image in the sequence has at least an ECG timing parameter associated therewith adequate to allow playback of the sequence in accordance with acquired real-time ECG signals obtained from ECG monitor 22. It should be understood that the foregoing are examples only and not limiting in nature. For example, the image database 18 may also include three-dimensional image data as well. It should be further understood that the images may be acquired through any imaging modality, now known or hereafter developed, for example X-ray, ultra-sound, computerized tomography, nuclear magnetic resonance or the like as well as a 3D geometry generated by the MPS itself.

MPS 20 is configured to serve as the localization system and therefore is configured to determine positioning (localization) data with respect to one or more of MPS location sensors $24_i$ (where i=1 to n) and output a respective location reading. The location readings may each include at least one or both of a position and an orientation (P&O) relative to a reference coordinate system 34, which may be a three-dimensional reference coordinate system associated with MPS 20. For example, the P&O may be expressed as a position (i.e., a coordinate in three axes X, Y and Z) and an orientation (i.e., roll, yaw and pitch) of a magnetic field sensor (e.g., sensor 24) in a magnetic field relative to a magnetic field generator(s) or transmitter(s). As will be described in greater detail below, MPS 20 is also configured to determine a P&O of an effective magnetic center 58 of distributed location sensor $24_1$ (see FIG. 3).

MPS 20 determines respective P&O readings in the reference coordinate system 34 based on capturing and processing signals (e.g., signal 36) received from the magnetic field sensors $24_i$ while such sensors are disposed in a controlled, low-strength magnetic field 38. From an electromagnetic perspective, these sensors develop a voltage that is induced on the sensor residing in a changing magnetic field. Sensors $24_i$ are thus configured to detect one or more characteristics of the magnetic field(s) in which they are disposed and generate a respective indicative signal (e.g., one shown—signal 36), which can be further processed by MPS 20 to obtain a respective P&O thereof. As mentioned above, sensor $24_1$ is a distributed location sensor.

FIG. 1 shows another MPS sensor, namely, patient reference sensor (PRS) $24_2$, which, if provided in system 10, is configured to provide a positional reference of the patient's body so as to allow motion compensation for gross patient body movements, imaging system movements and/or respiration-induced movements. PRS $24_2$ may be attached to the patient's manubrium sternum, a stable place on the chest, or another location that is relatively positionally stable. Like MPS sensor $24_1$, PRS $24_2$ is configured to detect one or more characteristics of the magnetic field in which it is disposed, and wherein MPS 20 provides a P&O reading indicative of the PRS's position and orientation in the reference coordinate system 34. In an embodiment, PRS $24_2$ can include three magnetic field location sensing coils configured to detect the PRS's location in six degrees of freedom (6DOF).

The electro-cardiogram (ECG) monitor 22 is configured to continuously detect an electrical timing signal of the heart organ through the use of a plurality of ECG electrodes (not shown), which may be externally-affixed to the outside of a patient's body. The timing signal generally corresponds to the particular phase of the cardiac cycle, among other things. Generally, the ECG signal(s) may be used by the main control unit 12 for ECG synchronized play-back of a previously captured sequence of images (cine loop) stored in database 18. ECG monitor 22 and ECG-electrodes may both comprise conventional components.

Figure 2:
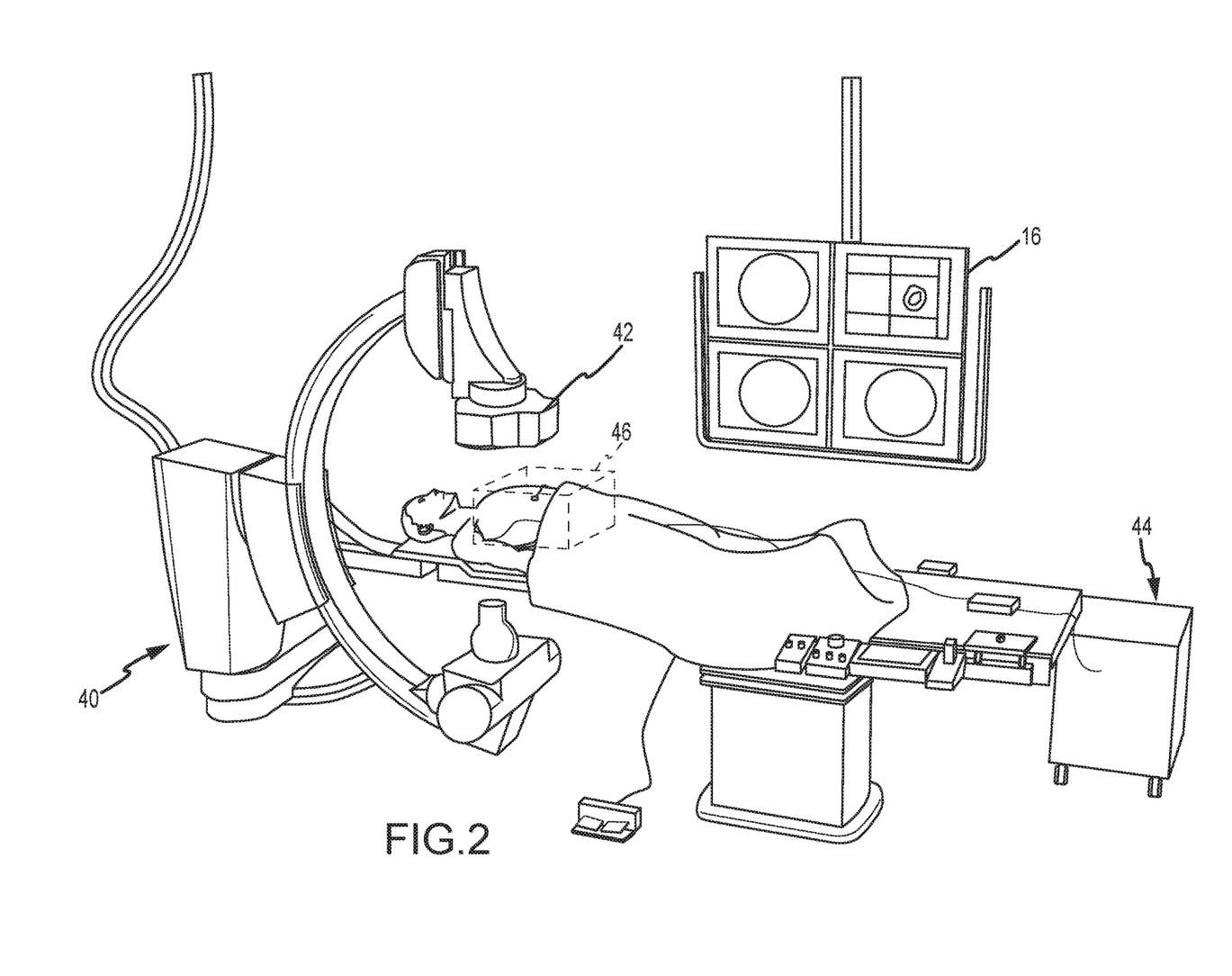
FIG. 2 is a diagrammatic view of an exemplary catheter lab environment in which the medical device of FIG. 1 may be used.

FIG. 2 is a diagrammatic view of system 10 as incorporated into an exemplary catheter laboratory. System 10 is shown as being incorporated into a fluoroscopic imaging system 40, which may include commercially available fluoroscopic imaging components. MPS 20 includes a magnetic transmitter assembly (MTA) 42 and a magnetic processing core 44 for determining location (P&O) readings. In an embodiment, the MTA 42 may be incorporated into the fluoroscopic imaging system by inclusion into the C-arm, for example as shown. In another embodiment, MTA 42 may be placed in other locations (e.g., not incorporated into the imaging system), such as, for example, under the patient table. MTA 42 is configured to generate the magnetic field(s) in and around the patient's chest cavity, in a predefined three-dimensional space identified as a motion box 46. MPS sensors $24_i$ as described above are configured to sense one or more characteristics of the magnetic field(s) and when the sensors are in motion box 46, each generate a respective signal that is provided to magnetic processing core 44. Processing core 44 is responsive to these detected signals and is configured to calculate respective P&O readings for each MPS sensor $24_i$ in motion box 46. Thus, MPS 20 enables real-time tracking of each sensor $24_i$ in three-dimensional space. One exemplary embodiment of MPS 20 will be described in greater detail below in connection with FIG. 10.

It should be understood that the computation of the sensor location is typically just an initial step, since it is frequently desired to then determine the device's spatial location (e.g., the location of the device's tip). To achieve this end goal, it is desirable to place the location sensor so as to lead to an accurate computation of the spatial location of the device. In many instances, it is thus desirable to place the location sensor at a symmetric position within the device (e.g., in a catheter, at the distal end on the longitudinal axis). However, in many instances, this desired position is already designated for another purpose (e.g., irrigation fluid delivery) and may therefore already be occupied by another structure (e.g., a fluid delivery lumen). Overall, the desired position for the location sensor is rarely available.

Figure 3:
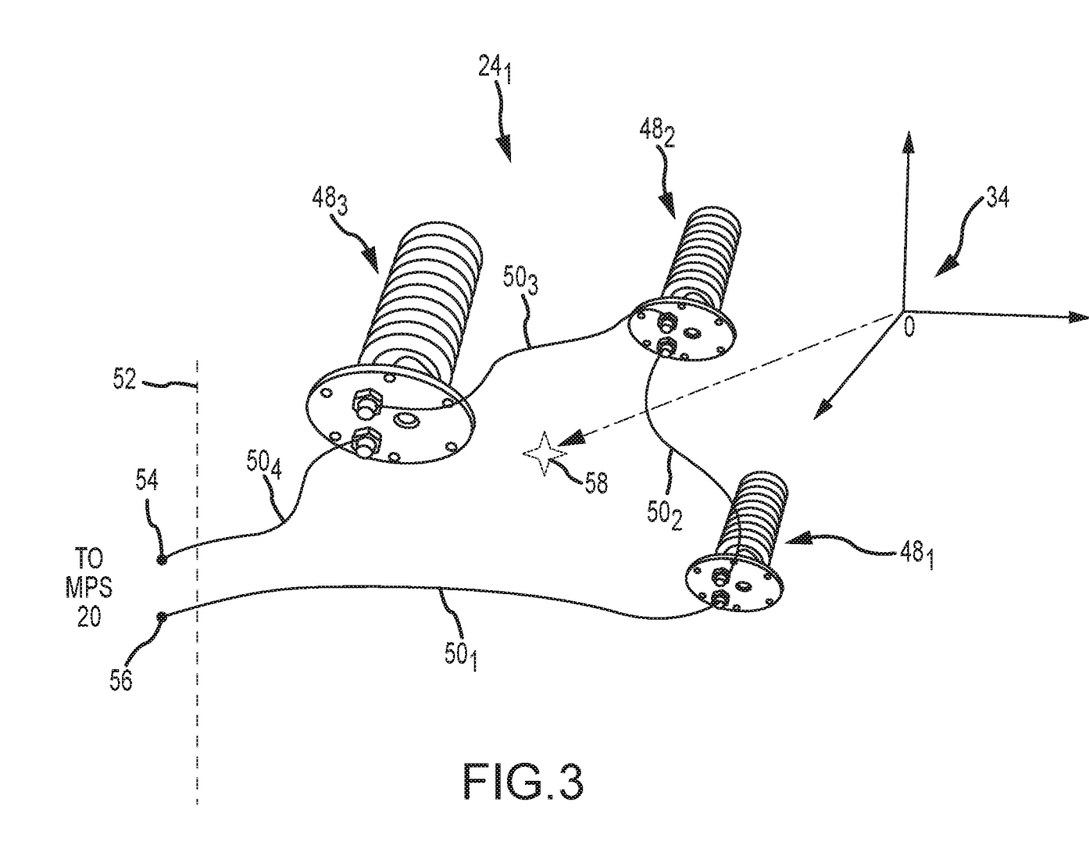
FIG. 3 is a diagrammatic view of an embodiment of a distributed location sensor.

FIG. 3 is a diagrammatic view of an embodiment of distributed location sensor $24_1$. As described above, restrictions on the size and placement of a magnetic field location sensor present challenges in the overall design of a medical device. Embodiments consistent with the instant disclosure involve embedding a plurality of sub-components of the sensor within the medical device in such a way that it bypasses the need to compete for sought-after space with other structures in the medical device. Instead of the conventional approach of first allocating a desired space for purposes of embedding a localization sensor, a different approach is taken where other structures are initially placed, and any remaining spaces (even if less desirable by conventional standards) are then allocated for deploying the sensing structure(s). Through this approach, components (or sub-components) that perform the sensing function are deployed "around" other functional structures in the device.

As mentioned above, MPS 20 is configured to determine a P&O of a sensor. In this regard, a typical sensor is a solid state component that includes an electrical conductor (e.g., wire) having a predetermined number of turns wound on a tube or a magnetically permeable (e.g., metal) rod or core. The sensor location represents an imaginary location, which is referred to herein as the effective center of the sensor. In a uniform sensor, the effective center will be aligned with the sensor's center of mass. These factors make placement of a conventional single-component sensor on-axis near the distal end of an elongated medical device desirable, so that the detected sensor location can be easily and accurately used to compute the tip location.

Because of the competition for space in a medical device, it is also desirable that the sensor be relatively small so as to increase the chances that it can be placed at an optimal location in the device (i.e., so that the computed sensor location can thereafter be used to accurately compute the location of the tip of the medical device). However, as the single-component sensor becomes smaller (e.g., a smaller coil), the induced signal is correspondingly reduced and can become subjected to noise.

In accordance with the present teachings, distributed location sensor $24_1$ uses a plurality of inducing sub-components such as coils, electrically connected in series, to realize a composite (and a spatially distributed) location sensor. Splitting the sensing function into a plurality of inducing sub-components, when electrically connected in series, allows for a reduction in size of each of the individual inducing components, thereby increasing the chances that each sub-component will be able to be placed in the device in any remaining space(s). In other words, since each of the individual inducing components is reduced in size, there is greater flexibility in their placement within the device. Moreover, electrically connecting the plurality of inducing coils in series means that the individual contributions from each inducing coil will be additive in the composite output signal, and thus the distributed location sensor can be used without compromising the overall signal strength.

Distributed location sensor $24_1$ is configured to produce a signal responsive to an applied magnetic field produced by a localization system (e.g., MPS 20) indicative of the location of an effective magnetic center 58 of the sensor $24_1$ in coordinate system 34. In an illustrative embodiment, sensor 24$_1$ includes a plurality of location sensing coils designated 48$_1$, 48$_2$, . . . , 48$_3$ that are electrically connected in series. Each location sensing coil 48$_i$ is a two-terminal device. A plurality of connecting wires 50$_1$, 50$_2$, 50$_3$, and 50$_4$ are provided to electrically connect location sensing coils 48$_i$ in series. As a result, distributed location sensor 24$_1$, despite being composed of a plurality of individual location sensing coils 48$_i$, still presents, with respect to an interface 52, as a two-terminal device, for example, having connecting lead ends 54, 56. The effective magnetic center 58 reflects the composite of the individual centers of the individual location sensing coils 48$_i$, which in turn is based on the individual detection characteristics of each location sensing coil 48$_i$. For example, the detection characteristics of a location sensing coil may be influenced by the coil size (e.g., diameter, longitudinal length), the wire size, the number of turns, the presence (or absence) of a core (i.e., magnetically-permeable material), the relative orientation of one coil relative to another coil, and other factors known in the art. In one embodiment, the particular, as-designed position of an effective magnetic center 58 within a medical device 26 may be improved as to accuracy through a post-manufacture and pre-use calibration procedure.

From a design perspective, the effective magnetic center 58 can be placed in a desired position within medical device 26 but which is already occupied by another structure. For example, such obstructions, for purposes of location sensor placement, may include, without limitation, an on-axis irrigation fluid delivery lumen, an off-axis irrigation fluid delivery lumen, a pull wire lumen, a pull wire, a pull ring, an electrical conductor, a twisted pair (TP) cable, a lumen for a twisted pair (TP) cable, an irrigation passageway, as well as other structures known in the art of medical devices (e.g., a temperature sensor such as a thermocouple, electrical conductors, etc.).

Figure 4:
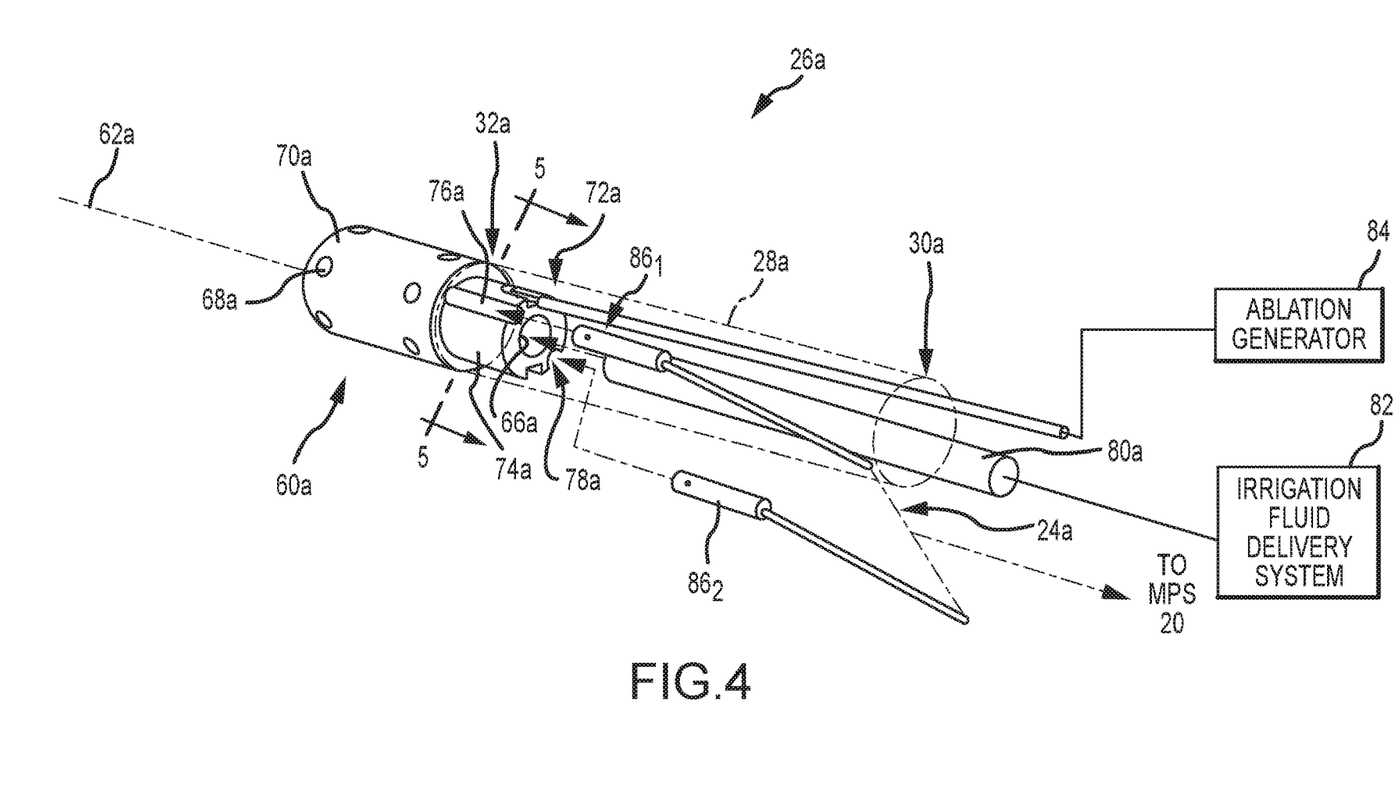
FIG. 4 is an exploded, isometric view of a distal portion of an irrigated ablation catheter that includes an embodiment of a distributed location sensor.

FIG. 4 is an exploded, isometric view of a distal portion of an irrigated ablation catheter 26*a* that includes an embodiment of a distributed location sensor, designated sensor 24*a*. Catheter 26*a*, thus equipped, is therefore configured for use with a magnetic field-based localization system, such as MPS 20. In the illustrated embodiment, catheter 26*a* includes a shaft 28*a* (shown in phantom line in FIG. 4 and best shown in FIG. 5) having a proximal end portion 30*a* and a distal end portion 32*a*.

In at least one embodiment, catheter 26*a* further includes a diagnostic and/or therapeutic element, such as an ablation tip electrode 60*a* located at distal end portion 32*a* of shaft 28*a*, and as shown has a longitudinal axis 62*a* associated therewith. Electrode 60*a* is configured generally for delivery of ablative energy, such as radio-frequency (RF) electrical current, to a target tissue site (e.g., the electrical current may flow from the electrode 60*a* through the target tissue site to another electrode, for example, a body surface electrode, patch electrode, another electrode on the catheter, or other electrodes as known). Electrode 60*a* may comprise conventional materials and configurations.

With continued reference to FIG. 4, electrode 60*a* also includes an irrigation passageway 64*a* (best shown in FIG. 5) with a fluid inlet 66*a* and at least one fluid outlet 68*a* on an outer surface 70*a* thereof. In the illustrated embodiment, electrode 60*a* may be configured with a plurality of fluid outlets 68*a* that are in fluid communication with irrigation passageway 64*a*. Outlets 68*a* (or "ports") are configured to eject irrigation fluid near and around (or on) outer surface 70*a* as well as on or around the warming-up tissue.

Electrode 60*a* further includes a proximal portion 72*a* having a reduced-diameter shank 74*a* configured to receive shaft 28*a*. Electrode 60*a* includes a first bore 76*a* axially extending into shank 74*a* and a second bore 78*a* extending into shank 74*a*. Bores 76*a*, 78*a* are configured to hold location sensing coils as described below.

Catheter 26*a* further includes an irrigation fluid delivery lumen 80*a* coupled at one end to fluid inlet 66*a*. Irrigation fluid delivery lumen 80*a* is configured to be coupled to an irrigation fluid delivery system 82 (e.g., at the other end opposite the end that is coupled to inlet 66*a*). When activated, irrigation fluid delivery system 82 pumps irrigation fluid through lumen 80*a*, which fluid is ultimately ejected from ports 68*a*. It should be understood, however, that the illustrated cooling structure(s) are exemplary only and not limiting in nature—other configurations and variations of irrigation passageways and/or fluid inlets/outlets are possible. As also shown, electrode 60*a* is electrically connected to an ablation generator 84, which is configured to control generation and delivery of ablative energy destined for electrode 60*a*.

Ablation catheter 26*a* illustrates the location sensor size and placement challenges described above. For example, the desired space for placement of a location sensing coil would be on-axis near electrode 60*a*; however, fluid delivery lumen 80*a* already occupies this on-axis space, and is therefore unavailable for use in placement of a location sensing coil. As will be described below, an embodiment consistent with the instant teachings provides for a distributed location sensor 24*a* that includes a plurality of sub-components, for example, first and second location sensing coils 86$_1$, 86$_2$ that are disposed, respectively, in first and second bores 76*a*, 78*a*.

First and second location sensing coils 86$_1$, 86$_2$ cooperate to perform the overall location sensing function, resulting in the ability of producing a signal indicative of the location of an effective magnetic center that resides in a space occupied by irrigation fluid delivery lumen 80*a* and may be coincident with the lumen's longitudinal axis (see longitudinal axis 62*a* in FIG. 5, discussed below). In addition, by breaking up the location sensor into sub-components, each sub-component (i.e., each one of the sensing coils 86$_1$, 86$_2$) can be reduced in size relative to a comparable single-coil sensor. This allows bores 76*a*, 78*a* to be sized so as to completely receive each coil 86$_1$, 86$_2$. This sizing approach prevents bulging of the shaft or other mechanical interference that could occur by attempting to fit a larger sensing coil into the same space. In other words, for example, a comparable single-coil sensor would not completely fit within a single bore, even if an off-axis placement were utilized, with the result that a portion of such a sensing coil would extend outside of the bore, causing space utilization complications.

Figure 5:
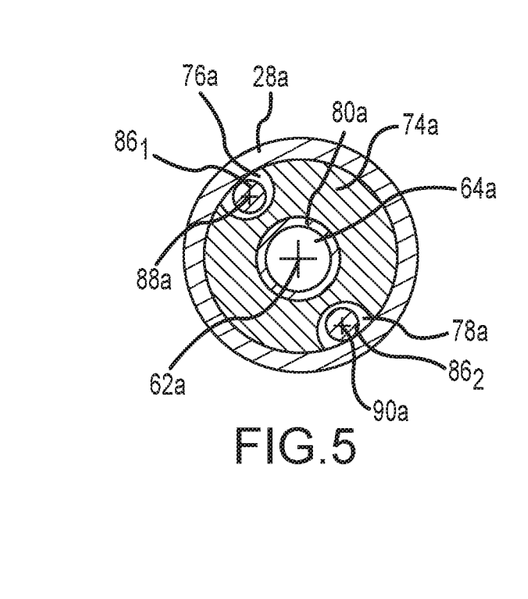
FIG. 5 is an enlarged, cross-sectional view of a portion of the catheter of FIG. 4 taken substantially along lines 5-5 when the catheter is assembled, showing a two-coil distributed location sensor embodiment.

FIG. 5 is an enlarged, cross-sectional view of a portion of catheter 26*a* taken substantially along lines 5-5 in FIG. 4 when the catheter is assembled. Each location sensing coil 86$_1$, 86$_2$ has a respective axis, designated 88*a*, 90*a* (the axes being directed into the paper). Neither one of axes 88*a*, 90*a* are coincident with longitudinal axis 62*a* on which lumen 80*a* is disposed. However, it should be appreciated that variations are possible. In this regard, in an alternate embodiment, at least one of the axes of the plurality of location sensing coils may be coincident with the longitudinal axis of the electrode/shaft. For example only, a distributed location sensor may include both an on-axis, hollow coil that surrounds a central irrigation fluid delivery lumen which would be co-axial therewith, in addition to the one or more of off-central-axis sensing coils described above. In addition, as shown, bores 76*a*, 78*a* may be radially offset from longitudinal axis 62a by substantially equal distances. In an alternate embodiment, the radial offset distances may be different. In addition, the respective detection characteristics of sensing coils $86_1$, $86_2$ may be either (i) the same; or (ii) different.

Figure 6A:
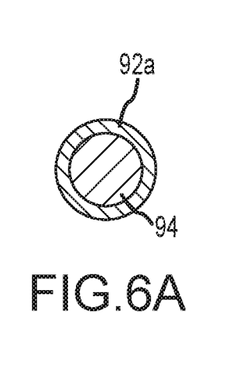
FIG. 6A is a cross-sectional view of a location sensing coil having a magnetically-permeable core.

FIG. 6A is a cross-sectional view of a location sensing coil that can be used in a distributed location sensor. In the illustrated embodiment, the location sensing coil includes a winding portion 92a wound on a solid core 94 that comprises magnetically permeable material. In an embodiment, solid core 94 can alternatively comprise non-magnetically permeable material.

Figure 6B:
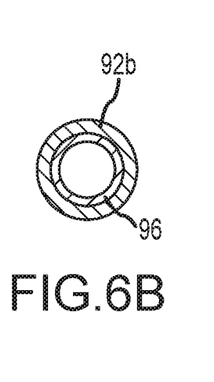
FIG. 6B is a cross-sectional view of a location sensing coil wound on a tube.

FIG. 6B is a cross-sectional view of another location sensing coil that can be used in a distributed location sensor. In the illustrated embodiment, the location sensing coil includes a winding portion 92a wound on a tube or spool 96 that can comprise non-magnetically permeable material. In an embodiment, spool 96 can comprise magnetically permeable material.

Figure 6C:
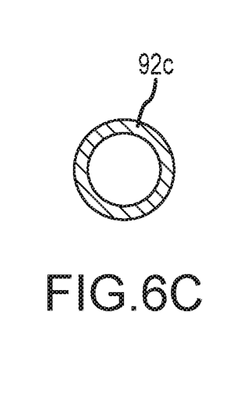
FIG. 6C is a cross-sectional view of a location sensing coil having an air core.

FIG. 6C is a cross-sectional view of another location sensing coil that can be used in a distributed location sensor. In the illustrated embodiment, the location sensing coil includes a winding portion 92c having no spool or core (i.e., an air core).

Figure 7:
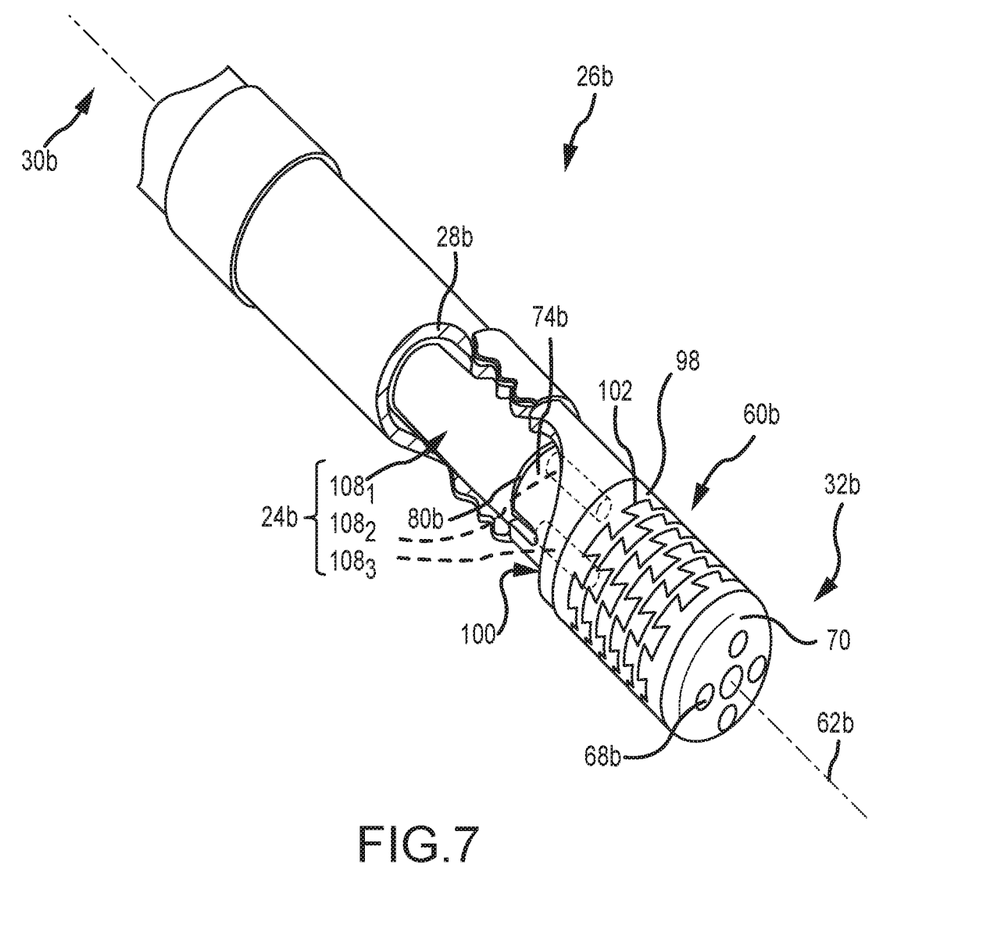
FIG. 7 is an isometric view, with portions broken away, of a distal portion of an irrigated ablation catheter with a bendable tip electrode that includes a further distributed location sensor embodiment.

FIG. 7 is an isometric view, with portions broken away, of an irrigated ablation catheter 26b with a bendable tip electrode. Catheter 26b includes a distributed location sensor 24b (best shown in FIG. 8 as coils $108_2$ and $108_3$) and is thus configured for use with a magnetic field-based localization system (e.g., MPS 20). Catheter 26b includes a shaft 28b having a proximal end portion 30b and a distal end portion 32b. Catheter 26b further includes an ablation tip electrode 60b at distal end 32b, which has a longitudinal axis 62b associated therewith. Electrode 60b is configured generally for delivery of ablative energy, such as radio-frequency (RF) electrical current, to a target tissue site (e.g., the electrical current may flow from the electrode 60b through the target tissue site to another electrode, for example, a body surface electrode or patch electrode, or other electrodes as known). Electrode 60b may comprise conventional materials and configurations, although as described above, may have a bendable tip as seen by reference to U.S. Pat. No. 8,187,267 (U.S. application Ser. No. 11/853,759, filed 11 Sep. 2007, herein the '759 application), and U.S. application Ser. No. 12/651,074, filed 31 Dec. 2009 (herein the '074 application). The '759 application and the '074 application are both hereby incorporated by reference as though fully set forth herein.

Figure 8:
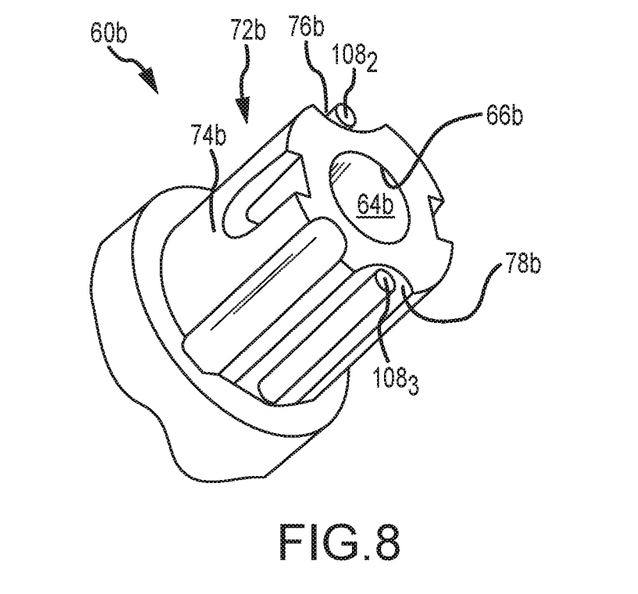
FIG. 8 is an isometric view of a shank portion of the tip electrode of FIG. 7 that includes a distributed location sensor embodiment.

FIG. 8 is an isometric view, with portions omitted for clarity, of a proximal end 72b of electrode 60b. Electrode 60b further includes an irrigation passageway 64b having a fluid inlet 66b and one or more fluid outlets 68b on an outer surface 70 (best shown in FIG. 7). Outlets 68b (or "ports") are configured to eject irrigation fluid near and around (or on) outer surface 70b. Electrode 60b includes a reduced-diameter shank 74b at proximal end 72b that is configured to receive shaft 28b on an outer surface thereof. As illustrated, electrode 60b includes a first bore 76b axially extending into shank 74b and a second bore 78b extending into shank 74b. Bores 76b, 78b are configured to hold location sensing coils as described in greater detail below.

With continued reference to FIG. 7, catheter 26b further includes an irrigation fluid delivery lumen 80b coupled at one end to fluid inlet 66b. Irrigation fluid delivery lumen 80b is configured to be coupled to irrigation fluid delivery system 82, as shown in FIG. 4 in block form. When activated, irrigation fluid delivery system 82 pumps irrigation fluid through lumen 80b, which fluid is ultimately ejected from port or ports 68b. Although not shown, electrode 60a is electrically connected to ablation generator 84, which is shown in FIG. 4 in block form. It should be understood, however, that the illustrated cooling structure(s) are exemplary only and not limiting in nature—other configurations and variations of irrigation passageways and/or fluid inlets/outlets are possible.

Electrode 60b also includes a sidewall 98 that defines an interior 100 (i.e., electrode 60b is hollow). Sidewall 98 has one or more elongated gaps 102 extending through sidewall 98. Gaps 102 are configured to provide flexibility in sidewall 98 for bending movement of electrode 60b relative to longitudinal axis 62b.

Figure 9:
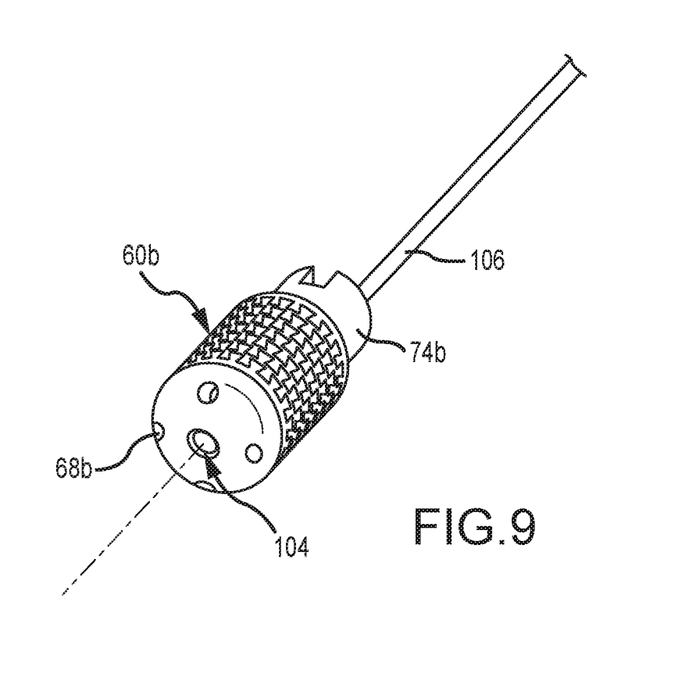
FIG. 9 is an isometric view, with portions omitted for clarity, of a distal portion of the catheter of FIG. 7 showing an obstruction that restricts placement of a location sensor.

Ablation catheter 26b, like ablation catheter 26a, also illustrates the size and placement challenges described above. For example, a structure in the form of lumen 80b is already located in the desired on-axis placement for a location sensing coil. Moreover, as shown in FIG. 9, catheter 26b includes additional restrictions on the placement of a location sensor, in the form of a thermocouple 104 and its corresponding connecting wires (not shown). A fluid lumen 106 is also shown. These items limit the available options with respect to the placement of a location sensing coil.

Referring now to FIGS. 7-8, distributed location sensor 24b of catheter 26b, in one embodiment, includes a hollow location sensing coil $108_1$ (FIG. 7) which is co-axial with longitudinal axis 62b, and which has an effective center at a desired location, namely, at a space occupied by fluid delivery lumen 80b. However, sensing coil $108_1$ may not be optimal for subsequent detection of the tip location, since the tip is bendable and the effective center of the coil $108_1$ may be too proximal to detect such bending. Accordingly, distributed location sensor 24b may further include, either as an addition to hollow sensing coil $108_1$, or in lieu thereof, at least a plurality of additional location sensing coils $108_2$, $108_3$.

In an embodiment, location sensing coil $108_1$ is omitted altogether and thus the distributed location sensor 24a includes the more distally-located first and second location sensing coils $108_2$, $108_3$, which are disposed, respectively, in first and second bores 76b, 78b as shown in FIG. 8. First and second location sensing coils $108_2$, $108_3$ together place an effective magnetic center in a space occupied by irrigation fluid delivery lumen 80a. In addition, splitting the location sensor into sub-components allows each sub-component (i.e., $108_2$, $108_3$) to be reduced in size, thereby allowing bores 76b, 78b to be sized so as to completely receive each coil $108_2$, $108_3$. This sizing approach may prevent or reduce bulging of the shaft or other mechanical interference that could occur by attempting to fit a larger sensing coil into the same space. In another embodiment, the location sensing coils are disposed such that the effective magnetic center resides at a location that allows detection of at least a part of the bendable portion of electrode 60b. In sum, embodiments of a distributed location sensor addresses the sizing and placement constraints described above that can exist in the design of a medical device.

Figure 10:
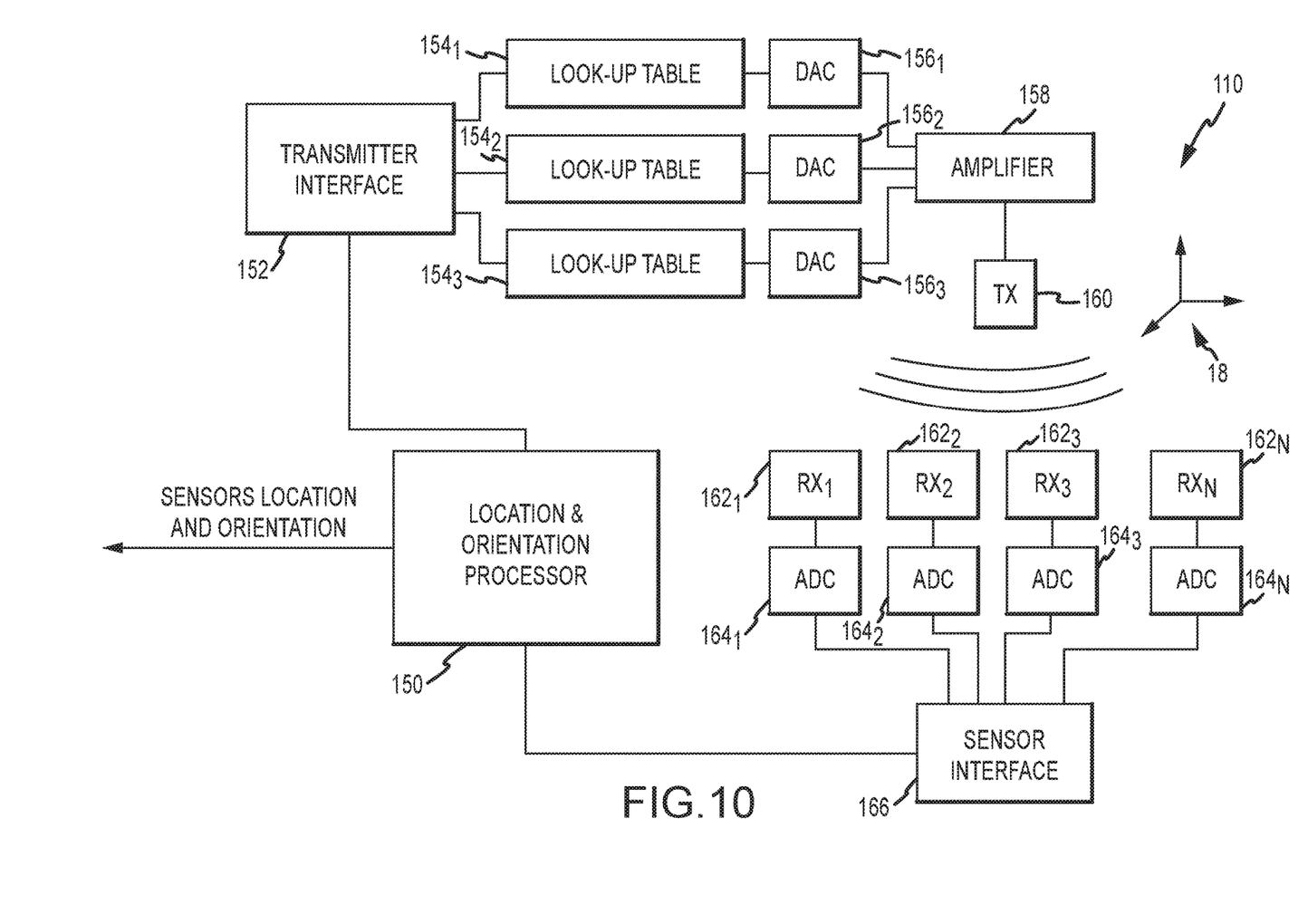
FIG. 10 is a schematic and block diagram view of an exemplary embodiment of a medical positioning system (MPS) that is shown in block form in FIG. 1.

FIG. 10 is a schematic and block diagram of one exemplary embodiment of MPS 20, designated as a MPS 110, as seen by reference to U.S. Pat. No. 7,386,339, hereby incorporated by reference as though fully set forth herein, having portions of which are reproduced below, which generally describes, at least in part, the MediGuide™ Technology system commercially offered by MediGuide Ltd. of Haifa, Israel and now owned by St. Jude Medical, Inc. It should be understood that variations are possible, for example, as also seen by reference to U.S. Pat. No. 6,233,476, hereby incorporated by reference as though fully set forth herein. Another exemplary magnetic field-based MPS is the Carto™ system commercially available from Biosense Webster, and as generally shown and described in, for example, U.S. Pat. Nos. 6,498,944, and 6,788,967, both hereby incorporated by reference as though fully set forth herein. Accordingly, the following description is exemplary only and not limiting in nature.

MPS 110 includes a location and orientation processor 150, a transmitter interface 152, a plurality of look-up table units $154_1$, $154_2$ and $154_3$, a plurality of digital to analog converters (DAC) $156_1$, $156_2$ and $156_3$, an amplifier 158, a transmitter 160, a plurality of MPS sensors $162_1$, $162_2$, $162_3$ and $162_N$, a plurality of analog to digital converters (ADC) $164_1$, $164_2$, $164_3$ and $164_N$ and a sensor interface 166.

Transmitter interface 152 is connected to location and orientation processor 150 and to look-up table units $154_1$, $154_2$ and $154_3$. DAC units $156_1$, $156_2$ and $156_3$ are connected to a respective one of look-up table units $154_1$, $154_2$ and $154_3$ and to amplifier 158. Amplifier 158 is further connected to transmitter 160. Transmitter 160 is also marked TX. MPS sensors $162_1$, $162_2$, $162_3$ and $162_N$ are further marked $RX_1$, $RX_2$, $RX_3$ and $RX_N$, respectively. In an embodiment, any one or more of the sensors $162_1$, $162_2$, $162_3$ and $162_N$ can in turn comprise a respective distributed location sensor, as described above. Analog to digital converters (ADC) $164_1$, $164_2$, $164_3$ and $164_N$ are respectively connected to sensors $162_1$, $162_2$, $162_3$ and $162_N$ and to sensor interface 166. Sensor interface 166 is further connected to location and orientation processor 150.

Each of look-up table units $154_1$, $154_2$ and $154_3$ produces a cyclic sequence of numbers and provides it to the respective DAC unit $156_1$, $156_2$ and $156_3$, which in turn translates it to a respective analog signal. Each of the analog signals is respective of a different spatial axis. In the present example, look-up table $154_1$ and DAC unit $156_1$ produce a signal for the X axis, look-up table $154_2$ and DAC unit $156_2$ produce a signal for the Y axis and look-up table $154_3$ and DAC unit $156_3$ produce a signal for the Z axis.

DAC units $156_1$, $156_2$ and $156_3$ provide their respective analog signals to amplifier 158, which amplifies and provides the amplified signals to transmitter 160. Transmitter 160 provides a multiple axis electromagnetic field, which can be detected by MPS sensors $162_1$, $162_2$, $162_3$ and $162_N$. Each of MPS sensors $162_1$, $162_2$, $162_3$ and $162_N$ detects an electromagnetic field, produces a respective electrical analog signal and provides it to the respective ADC unit $164_1$, $164_2$, $164_3$ and $164_N$ connected thereto. Each of the ADC units $164_1$, $164_2$, $164_3$ and $164_N$ digitizes the analog signal fed thereto, converts it to a sequence of numbers and provides it to sensor interface 166, which in turn provides it to location and orientation processor 150. Location and orientation processor 150 analyzes the received sequences of numbers, thereby determining the location and orientation of each of the MPS sensors $162_1$, $162_2$, $162_3$ and $162_N$. Location and orientation processor 150 further determines distortion events and updates look-up tables $154_1$, $154_2$ and $154_3$, accordingly.

It should be understood that system 10, particularly the main electronic control unit 12, as described above may include conventional processing apparatus known in the art, capable of executing pre-programmed instructions stored in an associated memory, all performing in accordance with the functionality described herein. Such an electronic control unit may further be of the type having both ROM, RAM, a combination of non-volatile and volatile (modifiable) memory so that any software may be stored and yet allow storage and processing of dynamically produced data and/or signals.

Although only certain embodiments have been described above with a certain degree of particularity, those skilled in the art could make numerous alterations to the disclosed embodiments without departing from the scope of this disclosure. Joinder references (e.g., attached, coupled, connected, and the like) are to be construed broadly and may include intermediate members between a connection of elements and relative movement between elements. As such, joinder references do not necessarily infer that two elements are directly connected/coupled and in fixed relation to each other. Additionally, the terms "electrically connected" and "in communication" are meant to be construed broadly to encompass both wired and wireless connections and communications. It is intended that all matter contained in the above description or shown in the accompanying drawings shall be interpreted as illustrative only and not limiting. Changes in detail or structure may be made without departing from the invention as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A medical device configured for use with a magnetic field-based localization system, comprising:
a shaft having a proximal end portion and distal end portion;
an element coupled to said distal end portion of said shaft configured to provide at least one of a diagnostic and therapeutic function, said element including a distal portion having a first outside diameter and a proximal portion including a shank having a second outside diameter that is reduced relative to said first outside diameter, said element further including a shoulder extending from a distal end of said shank to said distal portion, said element further having an irrigation passageway formed in a body portion of said shank of said element and wherein said irrigation passageway further includes at least one outlet on an outer surface of said distal portion of said element, and wherein said irrigation passageway further includes an inner surface in said body portion of said shank, said element including a first bore axially extending into said body portion of said shank and having a first inside surface, said element further including a second bore axially extending into said body portion of said shank and having a second inside surface, wherein said first and second inside surfaces are separated by said body portion, said irrigation passageway being separated from said first and second bores by said body portion; and
at least first and second location sensing coils being respectively disposed in said first bore and said second bore, said first and second location sensing coils being configured to produce a signal responsive to an applied magnetic field produced by the localization system, and wherein said at least first and second location sensing coils comprise cylindrical coils having a respective coil axis associated with a respective cylindrical axis thereof, and wherein said coil axes are radially offset from a longitudinal axis of said shaft.

2. The medical device of claim 1 further including a fluid delivery lumen coupled at one end thereof to said element, said lumen being configured to be coupled to an irrigation fluid delivery system.

3. The medical device of claim 1 wherein said shaft has a longitudinal axis, each of said sensing coils having a respective coil axis, wherein at least one of said coil axes is not coincident with said longitudinal axis.

4. The medical device of claim 1 wherein said at least first and second location sensing coils are off-central-axis relative to a central longitudinal axis of said shaft.

5. The medical device of claim 1 wherein said first and second bores are radially offset from said longitudinal axis of said shaft by a substantially equal distance.

6. The medical device of claim 1 wherein at least one of said location sensing coils includes a magnetically-permeable core.

7. The medical device of claim 1 wherein at least one of said location sensing coils comprises one of an air-core and a non-magnetically permeable core.

8. The medical device of claim 1 wherein the magnetic field-based localization system is configured to produce a three-dimensional location defined in a three-dimensional reference coordinate system responsive to said signal.

9. The medical device of claim 1 wherein said first location sensing coil has a first detection characteristic and said second location sensing coil has a second detection characteristic that is different from said first detection characteristic.

10. A medical device configured for use with a magnetic field-based localization system, comprising:
a shaft having a proximal end portion and distal end portion;
an element coupled to said distal end portion of said shaft configured to provide at least one of a diagnostic and therapeutic function, said element including a distal portion having a first outside diameter and a proximal portion including a shank having a second outside diameter that is reduced relative to said first outside diameter, said element further including a shoulder extending from a distal end of said shank to said distal portion, said element further including a first bore axially extending into a body portion of said shank and having a first inside surface, said element further including a second bore axially extending into said body portion of said shank and having a second inside surface, wherein said first and second inside surfaces are separated by said body portion;
an obstruction located on or in said shaft selected from the group comprising a fluid delivery lumen, a pull wire lumen, a pull wire, a pull ring, a twisted pair cable, an irrigation passageway, a temperature sensor, and electrical wiring; and
at least first and second location sensing coils being respectively disposed in said first bore and said second bore, said first and second location sensing coils being configured to produce a signal responsive to an applied magnetic field produced by the localization system, and wherein said at least first and second location sensing coils comprise cylindrical coils having a respective coil axis associated with a respective cylindrical axis thereof, and wherein said coil axes are radially offset from a longitudinal axis of said shaft.

11. The medical device of claim 10 wherein said shaft has a longitudinal axis, each of said sensing coils having a respective coil axis, wherein at least one of said coil axes in not coincident with said longitudinal axis.

12. The medical device of claim 10 wherein said at least first and second location sensing coils are off-central-axis relative to a central longitudinal axis of said shaft.

13. The medical device of claim 10 wherein said first and second bores are radially offset from said longitudinal axis of said shaft by a substantially equal distance.

14. The medical device of claim 10 wherein said first and second bores are radially offset from a longitudinal axis of said shaft by unequal distances.

* * * * *